US008889148B2

(12) United States Patent
Brown et al.

(10) Patent No.: US 8,889,148 B2

(45) Date of Patent: Nov. 18, 2014

(54) FLAVIVIRUS HOST-RANGE MUTATIONS AND USES THEREOF

(75) Inventors: Dennis T. Brown, Raleigh, NC (US); Raquel Hernandez, Raleigh, NC (US)

(73) Assignee: Research Development Foundation, Carson City, NV (US)

( * ) Notice: Subject to any disclaimer, the term of this patent is extended or adjusted under 35 U.S.C. 154(b) by 184 days.

(21) Appl. No.: 13/173,895

(22) Filed: Jun. 30, 2011

(65) Prior Publication Data

US 2012/0003255 A1 Jan. 5, 2012

Related U.S. Application Data

(60) Provisional application No. 61/360,645, filed on Jul. 1, 2010, provisional application No. 61/393,161, filed on Oct. 14, 2010.

(51) Int. Cl.

| | |
|---|---|
| ***A61K 39/12*** | (2006.01) |
| ***C07K 14/005*** | (2006.01) |
| ***C07H 21/04*** | (2006.01) |
| ***A61K 39/145*** | (2006.01) |
| ***C12N 7/00*** | (2006.01) |
| ***C12N 15/86*** | (2006.01) |
| *A61K 39/00* | (2006.01) |

(52) U.S. Cl.

CPC ........ *C12N 7/00* (2013.01); *C12N 2770/24171* (2013.01); *C12N 2770/24122* (2013.01); *A61K 39/12* (2013.01); *C12N 15/86* (2013.01); *C07K 14/005* (2013.01); *A61K 2039/525* (2013.01); *C12N 2770/24134* (2013.01); *C12N 2770/24145* (2013.01); *C12N 2770/24162* (2013.01); *A61K 2039/5254* (2013.01)

USPC ..................... 424/218.1; 530/350; 536/23.72; 424/204.1; 424/209.1

(58) Field of Classification Search

USPC ........................................................ 424/186

See application file for complete search history.

(56) References Cited

U.S. PATENT DOCUMENTS

| | | | | |
|---|---|---|---|---|
| 6,306,401 B1 | 10/2001 | Brown et al. | .............. | 424/218.1 |
| 6,589,533 B1 | 7/2003 | Brown et al. | .............. | 424/205.1 |
| 7,128,915 B2 | 10/2006 | Hernandez et al. | ........ | 424/199.1 |
| 7,335,363 B2 | 2/2008 | Hernandez et al. | ........ | 424/199.1 |
| 7,459,160 B2 | 12/2008 | Monath et al. | ........... | 424/199.1 |
| 2002/0106379 A1 | 8/2002 | Hernandez et al. | ........ | 424/188.1 |
| 2004/0009469 A1 | 1/2004 | Apt et al. | .......................... | 435/5 |
| 2005/0053624 A1 | 3/2005 | Arroyo et al. | ............. | 424/218.1 |
| 2007/0087354 A1 | 4/2007 | Charneau et al. | ................ | 435/6 |
| 2007/0269458 A1 | 11/2007 | Guirakhoo et al. | ........ | 424/218.1 |
| 2008/0026004 A1* | 1/2008 | Hernandez et al. | ........ | 424/199.1 |
| 2009/0117149 A1 | 5/2009 | Wicker et al. | ............. | 424/199.1 |

FOREIGN PATENT DOCUMENTS

WO WO 2009/114207 6/2009

OTHER PUBLICATIONS

Bryant et al., Glycosylation of the dengue 2 virus E protein at N67 is critical for virus growth in vitro but not for growth in intrathoracically inoculated *Aedes aegypti* mosquitoes, 2007, Virology, 366:415-423.*

Mukhopadyay et al., A Structural Perspective of the Flavivirus Life Cycle, 2005, Nature Reviews, 3:13-22.*

Nilsson et al., Proline-induced disruption of a transmembrane alpha-helix in its natural environment, 1998, JMB, 284:1165-1175.*

Dengue hemorrhagic fever: Diagnosis, treatment, prevention and control. 2nd Edition. World Health Organization 1997. Printed in England.

Adams and Rose, "Structural requirements of a membrane-spanning domain for protein anchoring and cell surface transport," *Cell*, 41(3):1007-1015, 1985.

Allison et al., "Mutational evidence for an internal fusion peptide in flavivirus envelope protein E," *Journal of Virology*, 75(9):4268-4275, 2001.

Bowers et al., "Replication and tissue tropism of the alphavirus Sindbis in the mosquito *Aedes albopictus,*" *Virology*, 212(1):1-12, 1995.

Bretscher and Munro, "Cholesterol and the Golgi apparatus," *Science*, 261:1280-1, 1993.

Brown and Condreay, "Replication of the alphaviruses in mosquito cells," In: *The Togaviruses and Flavivirlia*. Schlesinger et al. (Eds.), 11(2/3):171-207, Plenum Press, NY, 1986.

Ceruso and Weinstein, "Structural mimicry of prolin kinks: tertiary packing interactions support local structural distortions," *J. Mol. Biol.*, 318(5):1237-1249, 2002.

Condreay and Brown, "Exclusion of superinfecting homologous virus by Sindbis virus-infected *Aedes albopictus* (mosquito) cells," *J. Virol.*, 58:81-6, 1986.

Eckels et al., "Modification of dengue virus strains by passage in primary dog kidney cells: preparation of candidate vaccines and immunization of monkeys," *Am. J. Trop. Med. Hyg.*, 69:12-16, 2003.

Hernandez et al., "A single deletion in the membrane-proximal region of the Sindbis virus glycoprotein E2 endodomain blocks virus assembly," *J. Virol.*, 74:4220-8, 2000.

Hernandez et al., "Deletions in the transmembrane domain of a sindbis virus glycoprotein alter virus infectivity, stability, and host range," *J. Virol.*, 77(23):12710-12719, 2003.

Hernandez et al., "Sindbis virus: propagation, quantification, and storage," *Curr. Protoc. Microbiol.*, 15:15B-1, 2005.

Li et al., "The flavivirus precursor membrane-envelope protein complex: structure and maturation," *Science*, 319:1830-1834, 2008.

Lobigs and Lee, "Inefficient signalase cleavage promotes efficient nucleocapsid incorporation into budding flavivirus membranes," *J. Virol.*, 78:178-86, 2004.

Lobigs et al., "Evidence that a mechanism for efficient flavivirus budding upregulates MHC class I," *Immunol. Cell Biol.*, 82:184-8, 2004.

(Continued)

*Primary Examiner* — Zachariah Lucas
*Assistant Examiner* — Barry A Chestnut
(74) *Attorney, Agent, or Firm* — Parker Highlander PLLC

(57) ABSTRACT

Methods and compositions concerning mutant flaviviruses with host-range phenotypes are provided. Nucleotide sequences that encode mutant flavivirus proteins are also provided. In certain aspects, viruses comprising these sequences display reduced replication in mammalian cells. In further aspects of the invention, flavivirus vaccine compositions and methods for vaccination against flavivirus infection are provided.

23 Claims, 2 Drawing Sheets

(56) References Cited

OTHER PUBLICATIONS

Martin et al., "Viremia and antibody response in green monkeys (*Chlorocebus aethiops sabaeus*) infected with dengue virus type 2: a potential model for vaccine testing," *Microbiol. Immunol.*, 53:216-223, 2009.
Martin et al., "Viremia and the magnitude of the immune response upon infection of green monkeys with dengue virus type 2 are strain-dependent," *Curr. Microbiol.*, 59:579-583, 2009.
Mathews et al., "Expanded sequence dependence of thermodynamic parameters improves prediction of RNA secondary structure," *J. Mol. Biol.*, 288:911-40, 1999.
Mitsuhashi et al., "Sterol-free eukaryotic cells from continuous cell lines of insects," *Cell Biol. Int. Rep.*, 7(12):1057-62, 1983.
Monath, "Pathobiology of the flaviviruses," In: *The Togaviridae and Flaviviridae*, Schlesinger et al. (Eds.), 375-440, Plenum Press, NY, 1986.
Mukhopadhyay et al., "A structural perspective of the flavivirus life cycle," *Nat. Rev. Microbiol.*, 3:13-22, 2005.
Murray et al., "Architects of assembly: roles of Flaviviridae non-structural proteins in virion morphogenesis," *Nat. Rev. Micro.*, 6:699-708, 2008.
PCT International Search Report and Written Opinion issued in International application No. PCT/US2011/042600, dated Mar. 21, 2012.
PCT International Search Report and Written Opinion issued in International application No. PCT/US2011/029598, dated Dec. 19, 2011.
Rice et al., "Characterization of serum resistance of *Neisseria gonorrhoeae* that disseminate. Roles of blocking antibody and gonococcal outer membrane proteins," *J. Clin. Invest.*, 70(1):157-67, 1982.
Samsa et al., "Dengue virus capsid protein usurps lipid droplets for viral particle formation," *PLoS Pathog.*, 5:e1000632, 2009.
Schlesinger and, Schlesinger, "Replication of Togaviruses and Flaviviruses," In: *Virology*, 2nd Ed., Fields et al. (Ed.), Raven Press, NY, pp. 697-712, 1990.
Von Heijne, "Proline kinks in transmembrane alpha-helices," *J. Mol. Biol.*, 218(3):499-503, 1991.
West et al., "Mutations in the endodomain of Sindbis virus glycoprotein E2 define sequences critical for virus assembly," *J. Virol.*, 80:4458-68, 2006.
Whitehead et al., "Prospects for a dengue virus vaccine," *Nature*, 5:518-528, 2007.
Zhang et al., "Visualization of membrane protein domains by cryo-electron microscopy of dengue virus," *Nature Structural Biology*, 10(11):907-912, 2003.
Zhang et al., "Susceptibility of the Sf9 insect cell line to infection with adventitious viruses," *Biologicals*, 22:205-13, 1994.
Hsieh et al., "The length of and nonhydrophobic residues in the transmembrane domain of dengue virus envelope protein are critical for its retention and assembly in the endoplasmic reticulum," *Journal of Virology*, 84:4782-4797, 2010.
Liu et al., "Recombinant dengue virus-like particles from *Pichia pastoris*: efficient production and immunological properties," *Virus Genes*, 40:53-59, 2010.
Office Action issued in U.S. Appl. No. 13/069,905, mailed Aug. 10, 2012.
Office Action issued in U.S. Appl. No. 13/069,905, mailed Sep. 18, 2012.
Response to Office Action and Declaration Under 37 C.F.R. § 1.132 submitted in U.S. Appl. No. 13/069,905, filed Feb. 14, 2013.
Tan et al., "Characterization of the dengue virus envelope glycoprotein expressed in *Pichia pastoris," Methods in Molecular Biology, Glycovirology Protocols*, 379:163-176, 2007.

* cited by examiner

E-T1 Domain: SWTMKILIGVIITWIG

M-T1 Domain: PGFTMMAAILAYTIG

SEQUENCE LISTING

```
<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Ser Trp Thr Met Lys Ile Leu Ile Gly Val Ile Ile Thr Trp Ile Gly
1               5                   10                  15


<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2

Ser Trp Leu Ser Arg Leu Met Ile Gly Ala Leu Cys Leu Trp Ile Gly
1               5                   10                  15


<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Ser Trp Ile Thr Gln Gly Leu Leu Gly Ala Leu Leu Leu Trp Met Gly
1               5                   10                  15
```

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Asn Trp Ile Val Lys Ile Leu Ile Gly Thr Ile Phe Leu Trp Leu Gly
1 5 10 15

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Ser Trp Ile Thr Gln Gly Leu Met Gly Ala Leu Leu Leu Trp Met Gly
1 5 10 15

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Gly Phe Met Met Lys Met Ile Ile Ser Leu Val Leu Ile Trp Phe Cys
1 5 10 15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Ser Trp Ile Ser Pro Gly Leu Leu Gly Ala Leu Leu Leu Trp Met Gly
1 5 10 15

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Gly Phe Leu Pro Arg Ile Leu Leu Gly Ile Ser Leu Ala Trp Leu Gly
1 5 10 15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Gly Phe Leu Gly Lys Leu Met Ile Ser Gly Val Leu Ile Trp Leu Cys
1 5 10 15

-continued

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Ser Trp Ile Thr Gln Gly Leu Leu Gly Ala Leu Leu Leu Trp Met Gly
1 5 10 15

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide

<400> SEQUENCE: 11

Gly Phe Leu Pro Lys Leu Leu Leu Gly Val Ala Leu Ala Trp Leu Gly
1 5 10 15

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Ser Trp Ile Thr Gln Gly Leu Leu Gly Ala Leu Leu Leu Trp Met Gly
1 5 10 15

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

Asn Trp Ile Thr Lys Val Ile Met Gly Ala Val Leu Ile Trp Val Gly
1 5 10 15

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide

<400> SEQUENCE: 14

Ser Trp Phe Ser Gln Ile Leu Ile Gly Thr Leu Leu Val Trp Leu Gly
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Ser Trp Thr Met Lys Ile Gly Ile Gly Ile Leu Leu Thr Trp Leu Gly
1 5 10 15

-continued

```
<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Ser Trp Ile Met Lys Ile Gly Ile Gly Val Leu Leu Thr Trp Ile Gly
1               5                   10                  15


<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Ser Trp Met Ile Arg Ile Leu Ile Gly Phe Leu Val Leu Trp Ile Gly
1               5                   10                  15
```

FLAVIVIRUS HOST-RANGE MUTATIONS AND USES THEREOF

CROSS-REFERENCE TO RELATED APPLICATIONS

This application claims priority to U.S. Provisional Application No. 61/360,645 filed Jul. 1, 2010 and U.S. Provisional Application No. 61/393,161 filed Oct. 14, 2010. The entire text of each of the above-referenced disclosures is specifically incorporated herein by reference without disclaimer.

BACKGROUND OF THE INVENTION

1. Field of the Invention

The present invention relates generally to virology and disease control. Specifically, the present invention relates to mutated arthropod vectored viruses and their uses as vaccines. In particular aspects, the present invention relates to improved flavivirus constructs for use in preparing vaccines.

2. Description of Related Art

Arthropod vectored viruses (Arboviruses) are viral agents that are transmitted in nature by blood-sucking insects. Arboviruses include members of the alpha-, flavi- and bunyaviridae. The family of flaviviruses includes approximately 60 enveloped, positive strand RNA viruses, most of which are transmitted by an insect vector. Many members of this family cause significant public health problems in different regions of the world (Monath, 1986). The genome of all flaviviruses sequenced thus far has the same gene order: 5'-C-preM-E-NS1-NS2A-NS2B-NS3-NS4A-NS4B-NS5-3'. The first three genes code for the structural proteins: the capsid (C), the premembrane protein (pre M) and the envelope protein (E).

By their very nature, flaviviruses, like other Arboviruses, must be able to replicate in the tissues of both the invertebrate insect and the mammalian host (Brown and Condreay, 1986, Bowers et al., 1995). Differences in the genetics, biochemical environment, and optimal growth temperatures of these two host cell systems provide a basis for the production of host-range mutant viruses which can replicate in one host but not the other.

Dengue virus is a positive-sense RNA virus belonging to the Flavivirus genus of the family Flaviviridae. Dengue virus is widely distributed throughout the tropical and semitropical regions of the world and is transmitted to humans by mosquito vectors. Dengue virus is a leading cause of hospitalization and death in children in at least eight tropical Asian countries (WHO, 1997. Dengue hemorrhagic fever: diagnosis, treatment prevention and control-2nd ed. Geneva: WHO). Currently, Dengue Fever and other flaviviruses are in resurgence in the United States. The U.S. Army and other government agencies have tried to produce vaccines against these viruses since the 1960s with little success. Thus, there is a need to develop flavivirus vaccines for humans.

SUMMARY OF THE INVENTION

Viruses that are transmitted in nature by blood-sucking insects are a major source of disease in man and domestic animals. Many such viruses have lipid membrane bilayers with associated integral membrane proteins. These viruses are hybrid structures in which the proteins are provided by the genetic information of the virus, and the membrane is the product of the host cell in which the virus is grown. Differences in the composition of the membranes of the mammalian and insect host are exploited in aspects of the present invention to produce viruses having mutations in the membrane-spanning domains of virus membrane proteins. Some of the mutants are capable of replicating and assembling normally in the insect host cell, but assemble poorly in the mammalian host cell. These host-range mutants could produce immunity to wild-type virus infection when used as a vaccine and represent a novel strategy for the production of vaccines against arthropod vectored, membrane-containing viruses, such as flaviviruses.

In certain aspects of the invention, there is provided a modified flavivirus envelope protein (E) comprising a mutated E protein N-terminal transmembrane domain (E-T1 domain), or an engineered nucleic acid comprising a sequence encoding a modified flavivirus envelope protein (E) comprising a mutated E protein N-terminal transmembrane domain (E-T1 domain). The mutation in the modified flavivirus E protein may inhibit the production or infectivity of a virus comprising the modified viral transmembrane protein in mammalian cells. The term "nucleic acid sequence" as used herein comprises both RNA and DNA sequences, consistent with usage of the term in the art. The modified transmembrane protein may be able to span or correctly integrate into the membrane of insect cells, but may exhibit a reduced ability to span or correctly integrate into the membrane of mammalian cells due to mutation of one or more amino acids in the viral transmembrane protein. In particular, the mutation may be in a transmembrane domain of a viral transmembrane protein. The virus comprising the modified viral transmembrane protein may be capable of infecting and producing progeny virus in insect cells. In some aspects, the virus will be capable of infecting mammalian cells; however, the virus may have a reduced ability to produce progeny in mammalian cells.

Thus, in accordance with the present invention, the mutation will preferably reside in a transmembrane protein of a flavivirus, for example, the envelope (E) protein of a flavivirus. The mutation may be in a transmembrane domain of the E protein, such as the E protein's N-terminal transmembrane domain (E-T1 domain).

A linear sequence of a transmembrane domain has a central amino acid defined as that amino acid residue that resides essentially at the center of the membrane-spanning amino acids. Thus, in the case of the flavivirus E-T1 domain, the central amino acid will most often be the amino acid closest to the center of the 16 amino acid transmembrane domain, i.e., the $8^{th}$ or $9^{th}$ amino acid. The central amino acid is Glycine (G) in most of the more common Flaviviruses (see, e.g., Table 1). Such flavivirus E-T1 transmembrane domains include predicted transmembrane domains based on primary sequences.

Alignment of representative flaviviruses from each of the primary groups that are the main human pathogens is shown in Table 1. The alignment of the representative flaviviruses as compared to Dengue virus serotype 2 (DV2) was performed by DNASTAR® Lasergene software, MegAlign program, using the Clustal W method. The E-T1 domain in Dengue virus serotype 2 (DV2) served as the basis for E-T1 sequence alignment and is predicted as amino acids 452 to 467 of the E protein (Zhang et al., 2003). Other flavivirus E-T1 sequences not shown herein can be determined by optimal sequence alignment to the E-T1 sequence(s) of any of the representative flaviviruses—e.g., by the Bestfit method—and the "central" amino acid may be determined accordingly.

TABLE 1

Flavivirus E-T1 Sequences (bold: central amino acid)

| Flavivirus | GenBank # | E-T1 SEQUENCE | SEQ ID NO: |
|---|---|---|---|
| Dengue 2 Virus | U87411 | $_{452}$SWTMKILI**G**VIITWIG$_{467}$ | 1 |
| Aroa Virus | AY632536 | $_{458}$SWLSRLMI**G**ALCLWIG$_{473}$ | 2 |
| Bagaza Virus | AY632545 | $_{458}$SWITQGLL**G**ALLLWMG$_{473}$ | 3 |
| Entebbe Bat Virus | DQ837641 | $_{446}$NWIVKILI**G**TIFLWLG$_{461}$ | 4 |
| Japanese Encephalitis Virus | M18370 | $_{457}$SWITQGLM**G**ALLLWMG$_{472}$ | 5 |
| Modoc Virus | AJ242984 | $_{440}$GFMMKMIISLVLIWFC$_{455}$ | 6 |
| Murray Valley Encephalitis Virus | AF161266 | $_{458}$SWISPGLL**G**ALLLWMG$_{473}$ | 7 |
| Omsk Hemorrhagic Fever Virus | AY193805 | $_{453}$GFLPRILL**G**ISLAWLG$_{468}$ | 8 |
| Rio Bravo Virus | AF144692 | $_{442}$GFLGKLMIS**G**VLIWLC$_{457}$ | 9 |
| St. Louis Encephalitis Virus | DQ525916 | $_{458}$SWITQGLL**G**ALLLWMG$_{473}$ | 10 |
| Tick-borne Encephalitis Virus | U27495 | $_{45}$3GFLPKLLL**G**VALAWLG$_{468}$ | 11 |
| West Nile Virus | DQ211652 | $_{457}$SWITQGLL**G**ALLLWMG$_{472}$ | 12 |
| Yellow Fever Virus | X03700 | $_{451}$NWITKVIM**G**AVLIWVG$_{466}$ | 13 |
| Zika Virus | AY632535 | $_{457}$SWFSQILI**G**TLLVWLG$_{472}$ | 14 |

In some aspects of the present invention, amino acids of the transmembrane domain are numbered by relative positions based on the central amino acid, which is numbered as position 0 (for example, G460 in Dengue 2 virus), wherein amino acids proceeding toward the N terminus from the central amino acid are numbered −1, −2, etc., and amino acids proceeding toward the C-terminus from the central amino acid are numbered +1, +2, etc. For the purposes of such aspects, the mutation may comprise a proline substitution of one or more amino acids in the E-T1 domain, such as the central amino acid (i.e., position 0). In other aspects, the mutation may comprise a proline substitution at position −1, −2, −3, −4, −6, −8, +2, +3, +4, +5, or +6.

Because of its distinctive cyclic structure, proline often occurs at "turns" in a protein's structure and may cause distortions in the secondary structure of a polypeptide or region of a polypeptide (Ceruso et al., 2002; von Heijne, 1991). Thus, in certain aspects of the invention, the substitution of a proline for a wild-type amino acid in a transmembrane domain (e.g., the E-T1 transmembrane domain) may cause the "effective membrane-spanning distance" of the mutated transmembrane domain to be shorter than the effective membrane-spanning distance of a wild-type transmembrane domain, as illustrated below for the E-T1 transmembrane domain:

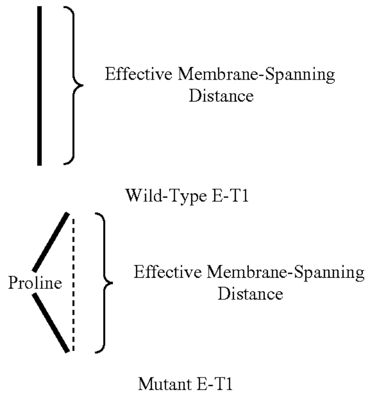

Non-limiting examples of flaviviruses include Dengue virus (DV), West Nile virus (WNV), yellow fever virus (YFV), Japanese encephalitis virus (JEV), tick-borne encephalitis virus (TBE virus), Murray Valley encephalitis virus (MVEV), Saint Louis encephalitis virus (SLEV), and Powassan virus (PV). Modified transmembrane proteins or engineered nucleic acid sequences comprising modified transmembrane proteins, especially a modified transmembrane domain, from each of these viruses is included as part of the present invention.

Some embodiments of the invention provide a modified flavivirus envelope protein comprising a mutation or an engineered nucleic acid comprising a sequence encoding a modified flavivirus envelope protein (E) comprising a mutation. Such a mutation may be in a transmembrane protein of the E protein, such as the E protein's N-terminal transmembrane domain (E-T1 domain). In certain aspects, the mutation in the E-T1 domain comprises a proline substituted for one or more amino acids at position 0, −1, −2, −3, −4, −6, −8, +2, +3, +4, +5, or +6. The mutation may comprise a proline substitution at position 0 of the E-T1 domain. The one or more mutations may cause the effective membrane-spanning distance of the mutated E-T1 domain to be shorter than the effective membrane-spanning distance of a wild-type E-T1 domain. In some embodiments, a virus comprising the modified flavivirus E protein has an ability to infect mammalian cells but a reduced ability to replicate therein relative to wild-type virus.

A modified flavivirus envelope protein or an engineered nucleic acid encoding a modified flavivirus envelope protein may comprise a modified flavivirus E protein of Dengue virus of type 1, 2, 3, or 4. In certain aspects, the modified flavivirus E protein is a modified E protein of Dengue virus type 2. In some embodiments, the modified E protein of Dengue virus type 2 comprises a mutation in the E-T1 domain, such as at position 0 (i.e., amino acid position 460).

In other aspects, the modified flavivirus E protein is a modified E protein of Dengue virus type 1 or Dengue virus type 4. The modified E protein of Dengue virus type 1 or type 4 may comprise a mutation in the E-T1 domain, such as at position 0 (i.e., amino acid 460). In further aspects, the modified flavivirus E protein is a modified E protein of Dengue virus type 3. The modified E protein of Dengue virus type 3 may comprise a mutation in the E-T1 domain, such as at position 0 (i.e., amino acid position 458).

The invention provides, in certain embodiments, a modified flavivirus envelope protein of West Nile virus or an engineered nucleic acid encoding a modified E protein of West Nile virus. In certain aspects, the modified E protein of West Nile virus comprises a mutation in the E-T1 domain, such as at position 0 (i.e., amino acid position 465).

The virus comprising the modified transmembrane protein such as flavivirus E protein may have an ability to produce at least or about 50, 100, 150, 200, 250, 300, 350, 400, 450, 500, 550, 600, 650, 700, 750, 800, 850, 900, 950, 1000, 5000, $10^4$ fold (or any range derivable therein) more progeny virus when infecting insect cells than when infecting mammalian cells. In certain aspects, the mammalian cells are human cells. In some aspects, the insect cells may be mosquito cells.

In some aspects, there is provided an engineered nucleic acid encoding a modified flavivirus envelope protein in accordance with aspects of the present invention. In other aspects, there is provided a genetically engineered flavivirus comprising at least one engineered nucleic acid in accordance with aspects of the present invention. Also provided are immunogenic compositions. Such an immunogenic composition may comprise at least one engineered nucleic acid in accordance with aspects of the present invention. In certain aspects of the immunogenic composition, the engineered nucleic acid may be comprised in a virus particle.

Such an immunogenic composition may be further defined as a vaccine composition in some aspects. In addition, the immunogenic composition may comprise an adjuvant, a preservative, or two or more viruses or nucleic acids, which are engineered in accordance with aspects of the invention. An immunogenic composition may comprise one or more modified flavivirus envelope proteins. The immunogenic composition may comprise one or more of a genetically engineered Dengue virus type 1, 2, 3, and 4. In certain specific embodiments, the immunogenic composition comprises a genetically engineered Dengue virus type 2. In other specific embodiments, the immunogenic composition comprises a tetravalent vaccine composition comprising the genetically engineered Dengue virus types 1, 2, 3, and 4.

Aspects of the invention may further include a method of producing a viral vaccine from a genetically engineered flavivirus for vaccination of mammals. Such a method of producing a viral vaccine may comprise introducing the genetically engineered virus to insect cells to produce a viral vaccine. Also provided is a method of inducing an immune response in a mammal, comprising administering the immunogenic composition to the mammal.

In a further embodiment there is provided a vaccine composition comprising one or more mutant flaviviruses, according to aspects of the invention, and a pharmaceutically acceptable excipient. Thus, it will be understood that the vaccine composition may comprise any of the mutant flaviviruses described herein. In further specific embodiments, a vaccine composition may comprise engineered nucleic acid sequences from two or more viruses according to the current invention. For example, the vaccine composition may comprise engineered sequences from four Dengue virus serotypes. In some embodiments, the mutant flavivirus is defective in assembly or infectivity in mammalian cells due to mutations in the transmembrane domain, but competent to assemble in or infect insect cells. In other embodiments the viruses may be further inactivated. For example, the viruses may be inactivated by irradiation or chemical treatment, such as formalin treatment. In further embodiments, vaccine compositions according to aspects of the invention may further comprise additional elements such as an adjuvant, an immunomodulator and/or a preservative.

In some further aspects of the invention, there is provided a method of vaccinating an animal comprising administering the vaccine composition to a mammal. The mammal may be a primate, and the primate may be a human. For example, in some specific embodiments the vaccine composition is administered to a human; however, the method may also be used to vaccinate livestock, wild and domesticated birds, cats, and dogs. In certain cases, the vaccine composition may be administered orally, intravenously, intramuscularly, intraperitoneally, or subcutaneously. In some cases, the vaccine composition is administered multiple times; and in certain cases, each administration is separated by a period of days, weeks, months or years. In other cases, the vaccine is administered in a single-dose administration.

Also provided is a composition for use in vaccinating a mammal for preventing flaviviral infections. The composition may be used, for example, to vaccinate a primate. In certain embodiments, the primate is a human. Such a composition may be administered intravenously, intramuscularly, intraperitoneally, or subcutaneously. In some aspects, the composition is to be administered two or more times. In other aspects, the composition is to be administered as a single dose.

Also provided is the use of a composition in the preparation of a medicament for vaccination of a mammal against flaviviral infections. In such a use, the mammal may be a primate, such as, for example, a human. In the context of such a use, the composition may be administered intravenously, intramuscularly, intraperitoneally, or subcutaneously. In some embodiments, the composition is to be administered two or more times. In other embodiments, the composition is to be administered as a single dose.

Embodiments discussed in the context of methods and/or compositions of the invention may be employed with respect to any other method or composition described herein. Thus, an embodiment pertaining to one method or composition may be applied to other methods and compositions of the invention as well.

As used herein, the terms "encode" or "encoding" with reference to a nucleic acid are used to make the invention readily understandable by the skilled artisan; however, these terms may be used interchangeably with "comprise" or "comprising" respectively.

As used herein in the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Introduction

Figure 1:
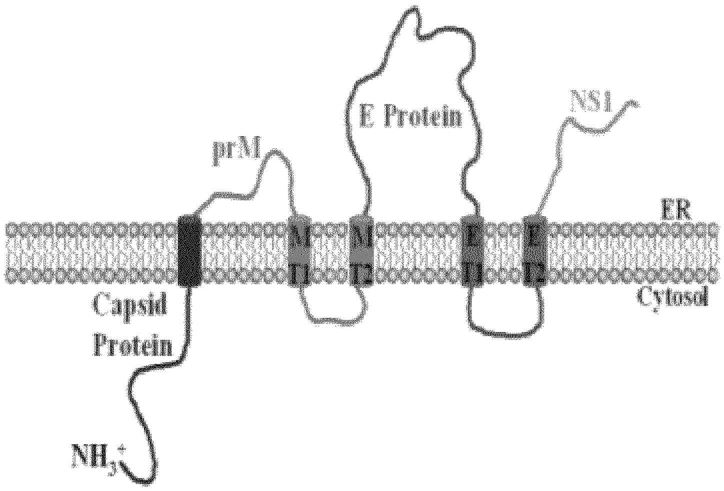
FIG. 1. Schematic representation of the organization of dengue virus structural proteins. Representation of DV protein structure illustrating the predicted orientation across the endoplasmic reticulum (ER). Cylinders represent transmembrane (T) helices; prM, membrane protein precursor; E, envelope protein; NS1, non-structural protein. The predicted sequences of the E protein T1 domain (E-T1) and M protein T1 domain (M-T1) of DV Type 2 are shown. The central amino acid of the DV Tvae 2 E-T1 domain is underlined.

There are over 700 known arboviruses and at least 80 immunologically distinct types that cause disease in humans. Arboviruses are transmitted among vertebrates by biting insects, chiefly mosquitoes and ticks. These viruses are widely distributed throughout the world, depending on the presence of appropriate hosts (birds, horses, domestic animals, humans) and vectors. Mosquito-borne arboviruses present some of the most important examples of emerging and resurgent diseases of global significance. A strategy has been developed herein by which host-range mutants of flaviviruses, such as Dengue virus, can be constructed by generating mutations in the transmembrane domain of the envelope (E) glycoprotein. The host-range mutants produced are restricted to growth in the insect hosts. This method of producing vaccine strains of arboviruses, such as flaviviruses, is novel, simple and inexpensive compared to other non-infectious vaccine platforms.

II. Definitions

As used herein, the term "membrane-bound virus" refers to a virus that contains a lipid membrane bilayer as part of its protective exterior coat.

As used herein the term "viral envelope" refers to the lipid membrane component of the membrane-containing virus and its associated proteins.

As used herein, the terms "arthropod vectored virus" or "Arbovirus" refer to viral agents that replicate and produce progeny virus in arthropod (insect) or mammalian cells. This includes members of the Togavirus, Flavivirus and Bunyavirus families. As used herein, the term "Togavirus" refers to a general classification of membrane-containing viruses that include the Alphaviruses.

As used herein, the term "membrane bilayer" refers to a structure consisting of opposed amphipathic phospholipids. The bilayer is organized in cross section from polar head groups to non-polar carbon chains to non-polar carbon chains to polar head groups.

As used herein, the term "transmembrane domain" refers to the amino acid sequence of the region of a membrane-integrated protein that spans the membrane bilayer.

As used herein, the term "effective membrane-spanning distance" means the effective distance that a transmembrane domain is able to stretch across a lipid bilayer. It will be appreciated by one of ordinary skill in this art that the "effective membrane-spanning distance" of a transmembrane domain may be reduced by introducing one or more mutations in the transmembrane domain. For example, one or more amino acids in the transmembrane domain may be deleted. In some embodiments, the structure of the transmembrane domain may be disrupted, such as by a kink introduced by substitution of a proline for one or more of the wild-type amino acids in the transmembrane domain.

As used herein, the term "viral vaccine" refers to a strain of virus or virus mutant or a combination of such viruses or virus mutants that has the antigenic properties of the virus but cannot produce disease.

As used herein the term "immune surveillance" refers to a process by which blood lymphocytes survey the cells and tissues of a mammal to determine the presence of foreign (virus) proteins and stimulates the production of lymphocytes capable of targeting cells producing the foreign protein for destruction. This process also leads to the production of circulating antibodies against the foreign protein.

As used herein, the term "infectious virus particles" refers to viruses that are capable of entering a cell and producing virus protein, whether or not they are capable of producing progeny virus.

As used herein, the term "non-infectious virus particles" refers to viruses that are not capable of infecting or entering a cell.

As used herein, the term "vertebrate cell" refers to any mammalian cell.

As used herein, the term "invertebrate cell" refers to any insect cell.

III. Flaviviruses

In certain aspects of the invention, there may be provided compositions and methods related to modification of flavivirus proteins for generating mutations that affect host-range phenotype. Therefore, flavivirus vaccines may be provided.

Flaviviruses are small, enveloped, positive-strand RNA viruses, several of which pose current or potential threats to global public health. Yellow fever virus, for example, has been the cause of epidemics in certain jungle locations of sub-Saharan Africa, as well as in some parts of South America. Although many yellow fever infections are mild, the disease can also cause severe, life-threatening illness. The disease state has two phases. The initial or acute phase is normally characterized by high fever, chills, headache, backache, muscle aches, loss of appetite, nausea, and vomiting. After three to four days, these symptoms disappear. In some patients, symptoms then reappear, as the disease enters its so-called toxic phase. During this phase, high fever reappears and can lead to shock, bleeding (e.g., bleeding from the mouth, nose, eyes, and/or stomach), kidney failure, and liver failure. Indeed, liver failure causes jaundice, which is yellowing of the skin and the whites of the eyes, and thus gives "yellow fever" its name. About half of the patients who enter the toxic phase die within 10 to 14 days. However, persons that recover from yellow fever have life-long immunity against reinfection. The number of people infected with yellow fever virus over the last two decades has been increasing. There are currently about 200,000 yellow fever cases, associated with about 30,000 deaths, each year. The re-emergence of yellow fever virus thus presents a serious public health concern.

Fully processed, mature virions of flaviviruses contain three structural proteins: capsid (C), membrane (M), and envelope (E). The infection also produces seven non-structural proteins. Immature flavivirions found in infected cells contain pre-membrane (prM) protein, which is a precursor to the M protein. The flavivirus proteins are produced by translation of a single, long open reading frame to generate a polyprotein, followed by a complex series of post-translational proteolytic cleavages of the polyprotein, to generate mature viral proteins (Amberg, 1999; Rice, 1995). The virus structural proteins are arranged in the polyprotein in the order C-prM-E (see FIG. 1).

Dengue Virus (DV), the most prevalent pathogenic arbovirus, is in the family Flaviviridae and has four distinct serotypes which cause an acute disease of sudden onset with headache, fever, prostration, severe joint and muscle pain, lymphadenopathy, and rash (Martina et al., 2009; WHO, 2009). DV is transmitted by mosquitoes. As distribution and density of mosquitoes has expanded, a considerable increase in Dengue virus transmission in tropical and subtropical areas throughout the world has been observed, with about 50 million cases of Dengue Fever and 500,000 cases of the more severe Dengue Hemorrhagic Fever (DHF). Over 20,000 deaths each year can be attributed to DHF, ranking Dengue with tuberculosis, STDs (including HIV), childhood diseases or malaria in costs of care and economic impact. DV is also the only known arbovirus that has fully adapted to the human host and has lost the need of an enzootic cycle for maintenance. The lack of prophylactics, vaccines or antivirals against DV alone leaves 2 billion people at risk yearly to contract this disease (WHO, 2009).

DV is an enveloped virus of 40 to 50 nm diameter with an icosahedral capsid that contains a single-stranded, positive sense RNA genome (Zhang et al., 2003). The envelope of DV is composed of hetero-dimers of the (E) glycoprotein and the membrane (M) protein that are embedded in a host-derived lipid bilayer (FIG. 1). The envelope surrounds the capsid, which is composed entirely of the capsid (C) protein encapsulating the RNA genome. The E glycoprotein is important for cell receptor attachment and infection of the target cell membrane, and it bears the neutralization epitopes (Mukhopadhyay et al., 2005). DV has, as have all arboviruses, evolved to replicate in the unique biochemical environments of both vertebrate and invertebrate hosts (Condreay and Brown, 1986). The mature viruses are hybrids that derive their lipid bilayers from the host cell. As compared to mammalian cell membranes, insect cell membranes contain very little cholesterol and are thinner in cross-section (Bretscher and Munro, 1993), Therefore, the membrane-spanning domains (transmembrane domains; TMDs) of proteins that must integrate into insect cell membranes and mammalian cell membranes have evolved to accommodate both host membranes.

In Sindbis—which is a structurally similar but distantly related Arbovirus—the E protein TMD can tolerate large deletions and thus was shown not to require the same effective membrane-spanning distance as those integrated into mammalian membranes (Hernandez et al., 2003). In Sindbis, this observation was used to develop a method for production of viral mutants comprising E proteins having truncated TMDs that were capable of efficient growth in invertebrate cells but incapable of efficient productive replication in vertebrate cells (Hernandez et al., 2003).

As demonstrated by studies herein, a targeted and rational method of mutating amino acids in the TMD of the envelope glycoproteins was used to create DV serotype 2 (DV2) mutants. Substituting a proline amino acid for one or more wild-type amino acids in the TMD of the E or M proteins of the virus will introduce proline kinks into such domains and decrease the effective membrane-spanning distance, such that the mutated domains are capable of spanning an insect cell membrane but not a mammalian cell membrane. As a result, viruses comprising such mutated E proteins will exhibit reduced infectivity in mammalian hosts but will retain efficient growth in insect hosts, thus producing a host-range phenotype. As discussed above, deletions in the TMD of Sindbis virus (SV), the prototypical arbovirus, resulted in viruses with altered infectivity and a host-range phenotype (Hernandez et al., 2003).

Both E and M proteins of DV have a TMD that can be targeted for mutation analysis using a proline-substitution strategy. In the study reported herein, mutant DV2 viruses were created and analyzed for a host-range phenotype restricted to growth in insect cells. Studies herein demonstrate that substitution of proline for an amino acid in the E protein TMD resulted in viruses having attenuated virulence in mammalian cells that retained the ability to grow in mosquito cells. Some proline-substitution mutants displayed little or no infectivity in insect or mammalian cells.

Additional flaviviruses that can be used in the invention include other mosquito-borne flaviviruses, such as Japanese encephalitis, Murray Valley encephalitis, St. Louis encephalitis, West Nile, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

In addition to the viruses listed above, as well as other flaviviruses, chimeric flaviviruses that include one or more mutations that decrease replication in mammalian cells are also included as a type of flavivirus in the invention. These chimeras can consist of a flavivirus (i.e., a backbone flavivirus) in which a structural protein (or proteins) has been replaced with a corresponding structural protein (or proteins) of a second virus (i.e., a test or a predetermined virus, such as a flavivirus). For example, the chimeras can consist of a backbone flavivirus (e.g., a yellow fever virus) in which the prM and E proteins of the flavivirus have been replaced with the prM and E proteins of the second, test virus (e.g., a dengue virus (serotypes 1-4), Japanese encephalitis virus, West Nile virus, or another virus, such as any of those mentioned herein). The chimeric viruses can be made from any combination of viruses. Preferably, the virus against which immunity is sought is the source of the inserted structural protein(s).

IV. Transmembrane Domain Mutations

In some aspects of the invention, a mutation is introduced into a transmembrane domain. Such a mutation may comprise the substitution of a proline (abbreviated as Pro or P) for one or more of the amino acids present in a wild-type transmembrane domain. Because of its distinctive cyclic structure, proline often occurs at "turns" in a protein's structure and may cause distortions in the secondary structure of a polypeptide or region of a polypeptide (Ceruso et al., 2002; von Heijne, 1991). Thus, insertion of a proline into a transmembrane domain would be expected to reduce the effective membrane-spanning distance in the mutant transmembrane domain as compared to a wild-type transmembrane domain. As explained below, the substitution of one or more prolines for one or more wild-type amino acids in the transmembrane domain may promote a host-range phenotype wherein the mutant virus can replicate in insect cells but exhibits a reduced ability to replicate in mammalian cells.

A proline mutation may be introduced by altering the wild-type nucleotide sequence, such as by altering the wild-type cDNA sequence. In a cDNA sequence, placement of a proline is dictated by the following codons: CCT, CCC, CCA, or CCG. Thus, mutation of a cDNA sequence to introduce one of those codons will provide a proline-substitution mutant.

The engineered nucleic acids of certain aspects of the present invention are based on mutations in the transmembrane domains of membrane glycoproteins of membrane-enveloped viruses, especially the E-T1 domain of flaviviruses. Many membrane-coated viruses have membrane glycoproteins on their surface that are responsible for identifying and infecting target cells (Schlesinger and Schlesinger, 1990). These membrane glycoproteins have hydrophobic membrane-spanning domains that anchor the proteins into the membrane bilayer (Rice et al., 1982).

The membrane-spanning domains of these transmembrane proteins need to be long enough to reach from one side of the bilayer to the other in order to hold or anchor the proteins in the membrane. Experiments have shown that if the domains are shortened by the deletion of amino acids within the domain, the proteins do not appropriately associate with the membrane and fall out (Adams and Rose. 1985).

As compared to mammalian cell membranes, the membranes of insect cells contain very little cholesterol that is obtained by diet (Clayton 1964, Mitsuhashi et al., 1983). Because insects have so little cholesterol in their membranes, the insect-generated viral membrane will be thinner in cross section than the viral membranes generated from mammals. Consequently, the membrane-spanning domains of proteins integrated into insect membranes do not need to be as long as those integrated into the membranes of mammals. It is possible, therefore, to produce engineered viruses with a transmembrane domain of the viral glycoprotein having a decreased effective membrane-spanning distance—e.g., by introducing one or more proline-substitution mutations or deletion mutations in the TMD. This process produces a glycoprotein that can integrate normally into the membrane of a virus replicating in an insect cell, but not into the membrane of a virus replicating, infecting, or assembling normally in a mammalian cell. Thus, the mutated virus can replicate and be produced in insect cells as well as the parent wild-type virus. On the other hand, the mutant virus can infect mammalian cells and produce viral proteins; however, since the mutated virus glycoprotein cannot span and be stably anchored in the mammalian membrane, progeny virus cannot be produced in mammalian cells to wild-type levels.

The methods and compositions described by the present invention may work for any virus that replicates in insects and mammals and has integral membrane proteins as part of its structure, such as Togaviruses, Flaviviruses, Bunyaviruses, and all other enveloped viruses that can replicate naturally in both mammalian and insect cells, as well as enveloped viruses that can be made to replicate in mammalian and insect cells by genetic engineering of either the virus or the cell.

Vaccines may be made against any membrane-containing virus by substituting one or more prolines for one or more wild-type amino acids in the membrane-spanning domain of a protein in the viral envelope. This is preferably done by altering a cDNA clone having the wild-type sequence, as described below. RNA transcribed from the altered clone may then be transfected into insect cells. The viruses produced are amplified by repeated growth in insect cells until large quantities of mutant viruses are obtained. These viruses are tested for the ability to infect and produce progeny in mammalian cells. Viruses that produce little to no progeny in mammalian cells are tested for the ability to produce immunity in laboratory animals. Those viruses that produce immunity in animal experiments are candidates for production of human and animal vaccines by procedures known in the art. Non-limiting examples of Flavivirus mutants are shown below in Table 2. Glycine (G) in the center of E-T1 transmembrane domain (amino acid G460 in Dengue serotypes 1, 2, & 4; aa G458 in Dengue 3; and aa G465 in West Nile virus) is designated as position zero in accordance with aspects of the present invention. As an example, a proline substitution mutation at the central Glycine (i.e., position 0) is described for each E-T1 sequence. However, it will be readily understood by persons skilled in this art that a proline-substitution mutation at a different amino acid position would similarly reduce the effective membrane-spanning distance of the E-T1. For example, proline may be substituted for one or more amino acids at position 0, −1, −2, −3, −4, −6, −8, +2, +3, +4, +5, or +6 (wherein the central amino acid of the E-T1 domain is numbered position 0, amino acids proceeding toward the N terminus are numbered −1, −2, etc., and amino acids proceeding toward the C-terminus are numbered +1, +2, etc.).

TABLE 2

Dengue and West Nile virus E-T1 Transmembrane Domain Mutants

| Clone | E-T1 Domain Sequence | Mutants |
|---|---|---|
| DEN2 | $_{452}$SWTMKILIGVIITWIG$_{467}$ (SEQ ID No: 1) | G460P |
| DEN1 | $_{452}$SWTMKIGIGILLTWLG$_{467}$ (SEQ ID No: 15) | G460P |
| DEN3 | $_{450}$SWIMKIGIGVLLTWIG$_{465}$ (SEQ ID No: 16) | G458P |
| DEN4 | $_{452}$SWMIRILIGFLVLWIG$_{467}$ (SEQ ID No: 17) | G460P |
| WNV | $_{457}$SWITQGLLGALLLWMG$_{472}$ (SEQ ID No: 12) | G465P |

In certain embodiments mutant viruses according to the current invention may comprise two or more mutations that independently or in combination promote a host-range phenotype. In some embodiments, mutant viruses additionally comprise other mutations such as attenuating mutations, mutations to increase immunogenicity or viral stability, or any mutations that may be used for vaccine production and that are currently known in the art.

V. Viral Vaccines

Certain aspects of the present invention are drawn to a method of producing a viral vaccine from genetically engineered membrane-enveloped viruses disclosed herein for vaccination of mammals, comprising the steps of introducing the engineered virus into insect cells and allowing the virus to replicate in the insect cells to produce a viral vaccine. Representative examples of the engineered viruses are Dengue virus E-T1 mutants (e.g., Dengue virus type 2 G460P).

Certain aspects of the invention regard host-range mutant viruses, such as those that produce a significant numbers of non-infectious virions. Such a host-range phenotype was associated with Sindbis virus mutants having a mutated transmembrane domain resulting in the domain having a reduced effective membrane-spanning distance. Sindbis virus is a member of alphavirus family. A significant difference in the assembly of alpha and flaviviruses is the association of the glycoprotein-modified viral membrane with the nucleocapsid. Alphaviruses are characterized by the strong association of the E2 tail with the nucleocapsid, which is required for assembly and infectivity (West et al., 2006). That strong association is absent in flaviviruses, and the mechanism by which virus budding occurs in association with the core is not known (Murray et al., 2008; Samsa et al., 2009). Additionally, flaviviruses produce empty particles (Lobigs and Lee, 2004; Lobigs et al., 2004; Murray et al., 2008), which increase toward late stages of infection suggesting that some component (viral or host) is depleted as the infection progresses. These specific differences in the details of virus assembly in the alpha and flavivirus systems underscore the importance of the membrane in the host-range phenotype. Thus, it is expected that this technology can be applied to other flaviviruses and arboviruses.

It is contemplated in certain aspects of the invention that one, two, three, four or more of these types of mutations can be combined, for example, to formulate a tetravalent vaccine. Furthermore, certain aspects of the present invention provide a method of producing a viral vaccine against a disease spread by a wild mosquito population to a mammal, comprising the steps of genetically engineering a mutation of one or more amino acids in a flavivirus E protein such as the E-T1 domain to produce an engineered virus, wherein the transmembrane protein is able to span the membrane envelope when the virus replicates in mosquito cells, but is unable to efficiently span the membrane envelope when the virus replicates in mammalian cells, and wherein the virus remains capable of replicating in mosquito cells; introducing the engineered virus into a wild mosquito population; and allowing the virus to replicate in cells of the wild mosquito population to produce a population of mosquitoes which excludes the wild-type pathogenic virus and harbors the vaccine strain of the virus such that a mosquito bite delivers the vaccine to a mammal that is bitten.

In addition, certain aspects of the present invention provide a method of vaccinating an individual in need of such treatment, comprising the steps of introducing the viral vaccine of the present invention into the individual and allowing the vaccine to produce viral proteins for immune surveillance and to stimulate the immune system for antibody production in the individual.

A. Vaccine Preparations

In any case, a vaccine component (e.g., an antigenic peptide, polypeptide, nucleic acid encoding a proteinaceous composition, or virus particle) may be isolated and/or purified from the chemical synthesis reagents, cell, or cellular components. A vaccine component may be cultured in a population of cells, such as a cell line. Any suitable cell population or cell line may be used. For example, a vaccine component (e.g., a polypeptide, a nucleic acid encoding a polypeptide, or a virus particle) may be cultured in insect cells. Suitable insect cells include, but are not limited to, C6/36 cells, Sf9 cells, other Sf series cells, *drosophila* S1 cells, other *drosophila* cell lines, or TN368 cells. It is anticipated that any cultured insect cells may be used to grow the vaccine components or viruses disclosed herein.

The C6/36 cell line (derived from *Aedes albopictus*) is made up of mosquito cells and is frequently used to study arboviruses, such as flaviviruses. C6/36 cells can be transfected with a vaccine component, such as a polypeptide or a nucleic acid encoding a polypeptide. The production of viruses can be visualized and monitored using a focus assay.

The Sf9 cell line (derived from *Spodoptera frugiperda*) is commonly used to express recombinant proteins and can be infected by viruses, including arboviruses. For example, Sf9 cells can be infected by viruses including recombinant baculovirus and St. Louis encephalitis, Yellow fever, DEN-1, DEN-2, Gumbo limbo, Eastern equine encephalomyelitis, herpes simplex virus type 1, and vesicular stromatitis viruses (Zhang et al., 1994). Yellow fever, DEN-1, and DEN-2 viruses can replicate in Sf9 cells (Zhang et al., 1994) such that Sf9 cells can be used to culture and produce such viruses.

In a method of producing a vaccine component, purification is accomplished by any appropriate technique that is described herein or well known to those of skill in the art (e.g., Sambrook et al., 1987). Although preferred for use in certain embodiments, there is no general requirement that an antigenic composition of the present invention or other vaccine component always be provided in their most purified state. Indeed, it is contemplated that a less substantially purified vaccine component, which is nonetheless enriched in the desired compound, relative to the natural state, will have utility in certain embodiments, such as, for example, total recovery of protein product, or in maintaining the activity of an expressed protein. However, it is contemplated that inactive products also have utility in certain embodiments, such as, e.g., in determining antigenicity via antibody generation.

Certain aspects of the present invention also provide purified, and in preferred embodiments, substantially purified vaccines or vaccine components. The term "purified vaccine component" as used herein, is intended to refer to at least one vaccine component (e.g., a proteinaceous composition, isolatable from cells), wherein the component is purified to any degree relative to its naturally obtainable state, e.g., relative to its purity within a cellular extract or reagents of chemical synthesis. In certain aspects wherein the vaccine component is a proteinaceous composition, a purified vaccine component also refers to a wild-type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s). For example, it is contemplated that immunomodulators can be included in the vaccine to augment a cell or a patient's (e.g., an animal's) response. Immunomodulators can be included as purified proteins, nucleic acids encoding immunomodulators, and/or cells that express immunomodulators in the vaccine composition.

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

Optionally, adjuvants that are known to those skilled in the art can be used in the administration of the viruses of the invention. Adjuvants that can be used to enhance the immunogenicity of the viruses include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In the case of a virus delivered via a mucosal route (for example, orally) mucosal adjuvants such as the heat-labile toxin of *E. coli* (LT) or mutant derivations of LT can be used as adjuvants. In addition, genes encoding cytokines that have adjuvant activities can be inserted into the viruses. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses.

An immunologic composition of the present invention may be mixed with one or more additional components (e.g., excipients, salts, etc.) that are pharmaceutically acceptable and compatible with at least one active ingredient (e.g., antigen). Suitable excipients are, for example, water, saline, dextrose, glycerol, ethanol and combinations thereof.

An immunologic composition of the present invention may be formulated into the vaccine as a neutral or salt form. A pharmaceutically acceptable salt, includes the acid addition salts (formed with the free amino groups of the peptide) and those that are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2 ethylamino ethanol, histidine, procaine, and combinations thereof.

In addition, if desired, an immunologic composition may comprise minor amounts of one or more auxiliary substances such as for example wetting or emulsifying agents, pH buffering agents, etc. that enhance the effectiveness of the antigenic composition or vaccine.

B. Vaccine Administration

Viruses of the invention can be administered as primary prophylactic agents in adults or children at risk of infection, or can be used as secondary agents for treating infected patients. For example, in the case of yellow fever/dengue chimeras, the vaccines can be used in adults or children at risk of Dengue infection, or can be used as secondary agents for treating Dengue-infected patients. Examples of patients who can be treated using the Dengue-related vaccines and methods of the invention include (i) children in areas in which Dengue is endemic, such as Asia, Latin America, and the Caribbean, (ii) foreign travelers, (iii) military personnel, and (iv) patients in areas of a Dengue virus epidemic. Moreover, inhabitants of regions where the disease has been observed to be expanding (e.g., Argentina, Chile, Australia, parts of Africa, southern Europe, the Middle East, and the southern United States), or regions where it may be observed to expand in the future (e.g., regions infested with *Aedes aegypti*), can be treated according to the invention.

Formulation of viruses of the invention can be carried out using methods that are standard in the art. Numerous pharmaceutically acceptable solutions for use in vaccine preparation are well known and can readily be adapted for use in the present invention by those of skill in this art (see, e.g., Remington's Pharmaceutical Sciences, $18^{th}$ Ed., 1990). In two specific examples, the viruses are formulated in Minimum Essential Medium Earle's Salt (MEME) containing 7.5% lactose and 2.5% human serum albumin or MEME containing 10% sorbitol. However, the viruses can simply be diluted in a physiologically acceptable solution, such as sterile saline or sterile buffered saline. In another example, the viruses can be administered and formulated, for example, in the same manner as the yellow fever 17D vaccine, e.g., as a clarified suspension of infected chicken embryo tissue, or a fluid harvested from cell cultures infected with the chimeric yellow fever virus. Preferably, virus can be prepared or administered in FDA-approved insect cells.

The vaccines of the invention can be administered using methods that are well known in the art, and appropriate amounts of the vaccines administered can readily be determined by those of skill in the art. For example, the viruses of the invention can be formulated as sterile aqueous solutions containing between $10^2$ and $10^7$ infectious units (e.g., plaque-forming units or tissue culture infectious doses) in a dose volume of 0.1 to 1.0 ml, to be administered by, for example, intramuscular, subcutaneous, or intradermal routes. In addition, because flaviviruses may be capable of infecting the human host via the mucosal routes, such as the oral route (Gresikova et al., 1988), the viruses can be administered by mucosal routes as well. Further, the vaccines of the invention can be administered in a single dose or, optionally, administration can involve the use of a priming dose followed by a booster dose that is administered, e.g., 2-6 months later, as determined to be appropriate by those of skill in the art.

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in creams, in lipid compositions (e.g., liposomes), or by other methods or any combination of the forgoing as would be known to one of ordinary skill in the art (see, for example, Remington's Pharmaceutical Sciences, $18^{th}$ Ed., 1990, incorporated herein by reference).

A vaccination schedule and dosages may be varied on a patient-by-patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1.5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed—and assays of protection from challenge with the flavivirus—can be performed following immunization.

Certain aspects of the present invention include a method of enhancing the immune response in a subject comprising the steps of contacting one or more lymphocytes with a flavivirus immunogenic composition, wherein the antigen comprises as part of its sequence a nucleic acid or amino acid sequence encoding mutant E protein, according to the invention, or an immunologically functional equivalent thereof. In certain embodiments the one or more lymphocytes is comprised in an animal, such as a human. In other embodiments, the lymphocyte(s) may be isolated from an animal or from a tissue (e.g., blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained from an animal (e.g., a patient), then pulsed with a composition comprising an antigenic composition. In a preferred embodiment, the lymphocyte(s) may be administered to the same or different animal (e.g., same or different donors).

VI. Pharmaceutical Compositions

It is contemplated that pharmaceutical compositions may be prepared using the novel mutated viruses of certain aspects of the present invention. In such a case, the pharmaceutical composition comprises the novel virus and a pharmaceutically acceptable carrier. A person having ordinary skill in this art readily would be able to determine, without undue experimentation, the appropriate dosages and routes of administration of this viral vaccination compound. When used in vivo for therapy, the vaccine of certain aspects of the present invention is administered to the patient or an animal in therapeutically effective amounts, i.e., amounts that immunize the individual being treated from the disease associated with the particular virus. It may be administered parenterally, preferably intravenously or subcutaneously, but other routes of administration could be used as appropriate. The amount of vaccine administered may be in the range of about $10^3$ to about $10^6$ pfu/kg of patient weight. The schedule will be continued to optimize effectiveness while balancing negative effects of treatment (see Remington's Pharmaceutical Science, 18th Ed., (1990); Klaassen In: Goodman and Gilman's: The Pharmacological Basis of Therapeutics, $8^{th}$ Ed. (1990); which are incorporated herein by reference). For parenteral administration, the vaccine may be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Production of Dengue Virus TM Domain Mutants

The TMDs of flaviviruses (including DV) E and M proteins are not precisely known; however they can be predicted with a high degree of certainty by sequence analysis (Rost et al., 2004). The TMDs of flaviviruses are shorter than those of alphaviruses, such as SV, (14-16 amino acids in flaviviruses as compared to 26-27 amino acids in alphaviruses) because the budding of the virus particles occurs from the ER in flaviviruses, which is thinner than the plasma membrane (Bretscher and Munro, 1993). However, like alphaviruses, flavivirus TMDs have no consensus sequence but model as hydrophobic helices. The shorter length of the flavivirus TMDs may require fewer mutations to produce the desired host-range phenotype. DV2 has two TMDs targeted for mutagenesis in this study: the first TMD of the E protein (E-T1), predicted to contain 16 amino acids, and the first TMD of the M protein (M-T1), calculated to contain 14 amino acids (Zhang et al., 2003). Substitution mutations were constructed, particularly proline-substitution mutations, and transcripts produced from each clone were transfected into cultured C6/36 (insect) cells and into cultured Vero (mammalian) cells as described below. Transfected cells were transferred to 24 well plates and incubated for 7 to 14 days at 28° C. At the end of the incubation period, the presence of virus was visualized by focus assay. In this assay, the quantity of foci is directly related to the efficiency of the transfection as well as the phenotype of the viral clone. Therefore the results determined identified mutants that may provide a host-range phenotype.

Analysis of the focus assay results confirmed the importance of the E-T1 and M-T1 domains in the assembly and expression of DV2. The focus assay enabled the visualization of infectious centers (foci) in the cells infected by the viral RNA. Based on number of foci, every mutant had greatly reduced expression from both Vero and C6/36 cells. It was observed that the G460P proline-substitution mutation (i.e., comprises a proline substituted for the wild-type glycine at amino acid 460 of the E protein in the E-T1 domain of Dengue virus type 2) provided a host-range phenotype (Table 3, below).

Thus, a primary screen can be utilized to identify preferred mutant viruses by a focus based immunostaining assay (Hernandez et al., 2005). Transcripts are generated for each DV2 mutant clone using a Ribomax kit as described in the methods. These transcripts are introduced into mosquito cells (C6/36) via electroporation. Transfected cells are plated in 24 well plates and incubated at 28° C. for C6/36 cells for 7, 10 and 14 days. The plates are developed, and foci indicate the production of infectious virus. The mutant viruses are then grown in both Vero and C6/36 cells to identify mutants that exhibit the desired host-range phenotype.

Methods

Cells and Viruses.

C6/36 cells (*Aedes albopictus*, obtained from ATCC, CRL-1660) were maintained in minimal essential medium (MEM) containing Earl's salts supplemented with 10% fetal bovine serum (FBS), 5% tryptose phosphate broth (TPB) and 2 mM L-glutamine. Vero cells (African Green monkey kidney, obtained from ATC, CCL-81) were maintained in 1×MEM supplemented with 10% FBS, 5% TPB, 2 mM glutamine 10 mM Hepes pH 7.4 and 1×MEM nonessential amino acids (NEAA) (1:100 dilution of NEAA from Gibco #11140).

Construction of DV2 Mutants.

A full-length cDNA clone of Dengue serotype 2 (DEN2; Thai strain 16681, GenBank #U87411) in pGEM3z+ was obtained from the Walter Reed Army Institute of Research for these studies (Irie et al., 1989). The clone produces full-length DEN2 RNAs when transcribed in vitro with T7 RNA polymerase and after transfection of the transcripts into mammalian or insect cells, infectious virions are generated.

Mutations in the TMD of the DEN2 E proteins were produced by polymerase chain reaction (PCR)-based site-directed mutagenesis, using Pfu Turbo® DNA polymerase AD (Stratagene, La Jolla, Calif.). Primers were designed to create proline-substitution mutations in the T1 domain of the E protein of DEN2. PCR conditions were as follows: 25 ng DEN2 DNA, 1× or 1.5×Pfu Turbo® Buffer, 0.4 mM/uL dNTPs (New England Biolabs, Ipswich, Mass.), 5 ng/uL each primer, and 0.1 U/uL Pfu Turbo® DNA polymerase AD. Reactions were run with and without DMSO (4% final concentration). PCR cycles were as follows: 95° C. for 2 min, then 25 cycles of 95° C. for 15 sec, 45 sec of annealing ($T_A$=Primer $T_m$−5° C. for each set of primers), 68° C. for 24 min. Extension was performed for 28 min at 68° C.; samples were held at 4° C. until analysis by gel electrophoresis. Following mutagenesis of the WT DEN2 clone, the PCR products were digested with DpnI (New England Biolabs) and transformed into SURE®2 Supercompetent *E. coli* cells (Stratagene) as per manufacturer's instructions with a few alterations. Following heat shock and recovery on ice, room temperature $NZY^+$ broth was added and incubation was performed at 30° C. After plating on Luria Broth (LB) agar containing 50 ug/mL carbenicillin (Teknova, Hollister, Calif.), incubation occurred at 30° C. for 36 to 48 hours. A colony PCR screen was then used to quickly identify the presence of the mutations in the resulting bacterial colonies prior to culture. Growth of all DEN2 clones in SURE®2 cells was conducted in LB containing 50 ug/mL carbenicillin at 28 to 30° C. for approximately 24 to 48 hours with shaking DEN2 plasmid DNA was recovered using Wizard® Plus Minipreps DNA Purification System (Promega, Madison, Wis.) following manufacturer's instructions. All DEN2 mutant clones were confirmed by sequence analysis (Eurofins MWG Operon, Huntsville, Ala.).

In Vitro Transcription and RNA Transfection.

Transcripts were generated for each DEN2 mutant clone using the RiboMAX™ Large Scale RNA Product Systems for T7 RNA Polymerase (Promega, Madison, Wis.) following manufacturer's instructions. The RNA transcripts were transfected into Vero and C6/36 cells as follows. Cells were pelleted and washed in RNase free electroporation buffer (PBS-D for Vero and MOPS for C6/36) and resuspended in their respective buffers at a concentration of 1-5×$10^7$ cell/ml. RNA transcripts were added to 400 μl of the cells and electroporated at 1.0 KV, 50 μF and ∞ resistance using Gene Pulsar II from BioRad. The transfected cells were then plated out at different concentrations in three different 24 well plates with 1.0 ml of the media and incubated at 37° C. for Vero cells and 28° C. for C6/36 cells for 1 hr with slow rocking. The media was removed and the plates overlayed with 1.0 ml of 1% carboxymethylcellulose (CMC) in 1× Vero media/1× C6/36 media and incubated for 7, 10 and 14 days. The plates were developed by focus assay on their respective days.

Virus Screen-Primary Screen:

A mutant virus screen based on a focus assay (a colorimetric focus assay or fluorescent focus assay) was developed to determine the infectivity of the virus. The screen was performed by first transcribing the linearized mutant DEN2 DNA clone into RNA as described previously (Hernandez et al., 2003). The RNA transcripts were transfected in Vero and C6/36 as described above. The transfected cells were then plated out at different concentrations in three different 24 well plates with 1.0 ml of the media and incubated at 37° C. for Vero cells and 28° C. for C6/36 cells for 1 hr with slow rocking. The plates were overlayed with 1.0 ml of 1% CMC in 1× Vero media or 1× C6/36 media and incubated for 7, 10 and 14 days. The foci on the plates were developed by color focus assay on their respective days. The cells were fixed on the respective days (see above). Foci are then counted and a titer determined in focus forming units/ml (ffu/mL) of virus. Each focus represents an infectious center demonstrating that the virus is able to infect the neighboring cells.

Virus Screen-Secondary Screen:

For the second screen the RNA transcripts for the mutant viruses selected after the first round of screening, are transfected again into C6/36 cells and transferred to 25 $cm^3$ flasks and incubated at 28° C. for 7 days. The virus is harvested and amplified once by infecting another flask of C6/36 cells. The virus is harvested on day 7 of infection and titrated using either Vero or C6/36 cells as indicator cells. Serial viral dilutions are made with dilution buffer (PBS-D+3% FBS) and 200 μl of the virus of each of the dilutions is used to infect the cell monolayers in 24 well plates for 1 hr at 37° C. The infected cell monolayers are overlayed with 1.0 ml of 1% CMC in 1× Vero media or 1× C6/36 media and incubated at their respective temperatures for 7 days and foci are developed by focus assay as described above. Once a measurable titer is observed for any of the mutant viruses, it is used to infect Vero and C6/36 cell lines at an MOI (multiplicity of infection) of ~0.03. The virus is harvested on day 7 and is titrated in a similar way as described above on both the Vero and C6/36 cell lines to distinguish the host-range phenotype.

Example 2

Host-Range Mutants of DV2

The DV2 mutants were used to infect both Vero and C6/36 cells at a known MOI to look for a host-range phenotype. The Vero and C6/36 cells were infected with the mutants at MOI ~0.03 FFU. The mutant viruses were grown in each cell line, harvested on day 7 and titered on Vero cells to look for the host-range phenotype. The results of this experiment are shown in Table 3. The A46P and M45P M-T1 mutants were unable to produce viral progeny in C6/36 cells. The M455P and V461P E-T1 mutants were also unable to produce viral progeny in C6/36 cells. The G460P, G467P, and W453P mutants produced viral progeny in C6/35 cells, and thus were tested in the second screen to determine if any of these mutants exhibits a host-range phenotype. The G460P mutant exhibited a host-range phenotype, producing a virus titer of 1×$10^3$ in insect cells and no measurable virus titer in mammalian cells.

TABLE 3

| DEN2 Mutants Tested | | | |
|---|---|---|---|
| | First Screen (C6/36) Infectious virus | Second Screen Vero | C6/36 |
| Wild type DEN2 ET1 $_{452}$SWTMKILIGVIITWIG$_{467}$ (SEQ ID NO: 1) | | 1 × $10^6$ ffu/ml | 1 × $10^7$ ffu/ml |

TABLE 3-continued

| DEN2 Mutants Tested | First Screen (C6/36) Infectious virus | Second Screen Vero | C6/36 |
|---|---|---|---|
| DEN2ET1, $G_{460}$→P | + | – | $1 \times 10^3$ ffu/ml |
| DEN2ET1, $M_{455}$→P | – | nd | nd |
| DEN2ET1, $V_{461}$→P | – | nd | nd |
| DEN2ET1, $G_{467}$→P | + | $1.5 \times 10^3$ ffu/ml | $1 \times 10^2$ ffu/ml |
| DEN2ET1, $W_{453}$→P | + | 5 ffu/ml | 5 ffu/ml |
| DEN2MT1, $A_{46}$→P | – | nd | nd |
| DEN2MT1, $M_{45}$→P | – | nd | nd |

In order to analyze the differences in virus production between mammalian and mosquito cells, thin sections of cells infected with wild type and mutant viruses were prepared and evaluated by electron microscopy. Infectious virus particles were seen in large paracrystalline structures within the mosquito cell and associated with the mammalian plasma cell membrane. Both wild-type virus and the G460P mutant virus exhibited virus production in mosquito cells. In mammalian cells, however, the G460P mutant exhibited defects in production of viral progeny.

To evaluate the amount of infectious virus produced by the G460P mutant, the number of focus-forming units (ffu) per mL was measured and compared to two other host-range mutants. The AGVII mutant, which has a deletion at amino acids 460 to 463 of the Den 2 E-T1 domain (i.e., positions 0 to +3), produced $1.5\times10^4$ ffu/mL. The ΔLIG mutant, which has a deletion at amino acids 458 to 460 of the Den 2 E-21 domain (i.e., positions −2 to 0), produced $5\times10^3$ ffu/mL. The G460P Den 2 E-T1 domain mutant produced $1.5\times10^5$ ffu/ml. Thus, the G460P mutant produced more infectious virus than the ΔGVII or ΔLIG mutant.

The G460P host-range mutant virus was tested to determine whether or not it reverts to wild-type viruses in C6/36 cells over serial passages, e.g., four serial passages. The cell culture supernatant was collected from the infection after each round of infection, and the sequence of viral RNA was analyzed by RT-PCR as described above. After four serial passages, the G460P mutant did not revert to wild-type.

To evaluate the immunogenicity, safety, and efficacy of a vaccine against DEN2, immunization experiments were performed in African green monkeys. African green monkeys provide a useful model for the preclinical assessment of novel candidates for Dengue vaccines (Martin et al., 2009; Martin et al., 2009). In the present study, serum samples were collected and clinical observations made at baseline and at 1, 2, 3, 5, 7, 14, 30 and 60 days after vaccine administration. After serum collection on day 60 animals received live DEN-2 challenge virus (wild type 16803); 4-5 log 10 PFU per animal) before continued serum collection and clinical observations at 61-67 and 74 days post-vaccine administration. All animals were prescreened for the presence of anti-Dengue 1-4 IgM or IgG.

Viremia was found to peak at day 2-3 post-injection for all test viruses. Table 4 shows the maximum viremia titer for each monkey expressed as infectious centers/mL (Edwards and Brown, 1991). An assay of infectious centers was chosen over a plaque assay because the infectious center assay is more sensitive. No viremia was detected in the mock-infected controls. The assay for production of neutralizing IgM and IgG titers began on day 5 post-injection and included days 7, 14 and 30 (Table 4). Three different assays to test for Ab production were performed on each individual sample in each group on the days reported.

TABLE 4

Maximum viremia and observed Ab titers

| | Animal ID | Weight | Inoculum | Max Viremia | Observed Antibody Titers Pre Challenge Day 0 | Day 5 | Day 7 | Day 14 | Day 30 |
|---|---|---|---|---|---|---|---|---|---|
| 2 | R349 | 3.82 | Neg. Control | 0 | 0 | 0 | 2560 | 20 (160) | 40 (0) |
| 6 | X073 | 5.32 | Neg. Control | 0 | 0 | 40 | 0 | 160 (0) | 0 (0) |
| 8 | X161 | 4.64 | Neg. Control | 0 | 0 | 80 | 0 | 80 (0) | 0 (0) |
| 12 | X608 | 4 | Neg. Control | 0 | 0 | 0 | 0 | 640 (0) | 0 (0) |
| 3 | R230 | 4.14 | G460p | 2.40E+04 | 0 | 0 | 0 | 640 | 0 (0) |
| 7 | X144 | 3.66 | G460p | 1.20E+04 | 20 | 0 | 0 | 640 (320) | 0 (0) |
| 10 | X395 | 4.5 | G460p | 2.80E+02 | 0 | 2560 | 0 | 0 | 0 (0) |
| 14 | X898 | 5.36 | G460p | 8.00E+02 | 40 | 0 | 0 | 320 (320) | 640 (640) |
| 11 | X403 | 4 | LAV (16803) | 1.60E+04 | 0 | 0 | 0 | 40 (320) | 0 (80) |
| 13 | X667 | 3.97 | LAV (16803) | 1.20E+03 | 0 | 0 | 0 | 640 (20) | 320 (20) |
| 17 | Y340 | 4.83 | LAV (16803) | 1.50E+02 | 0 | 640 | 160 | 640 (80) | 640 (160) |
| 19 | Y557 | 5.1 | LAV (16803) | 1.60E+04 | 0 | 40 | 20 | 640 (20) | 80 (20) |

These data show the peak viremia titer and antibody titer for each individual animal. Also shown are data from a plaque reduction neutralization assay (PRNT) and represent the inverse of the serum dilution in which 50% of the control DV2 virus was inhibited. The numbers in parentheses are from a focus reduction neutralization assay (FRNT) and also represent the dilution at which 50% inhibition was observed. Monkeys tested positive for IgM on days 5, 7 and 14 or IgG on days 14 and 30.

The data shown in Table 4 demonstrate that each individual monkey responded differently to the inoculation, although each group followed a notable trend. Of note is monkey 10, which peaked in Ab production on day 5 only. In general, the mutants began to produce Ab on day 5 compared to the control (DV2 16681), which peaked at day 14. Ab production pre-challenge appears to peak on day 14, both IgM and IgG with some IgG still detectable on day 30.

Figure 2:
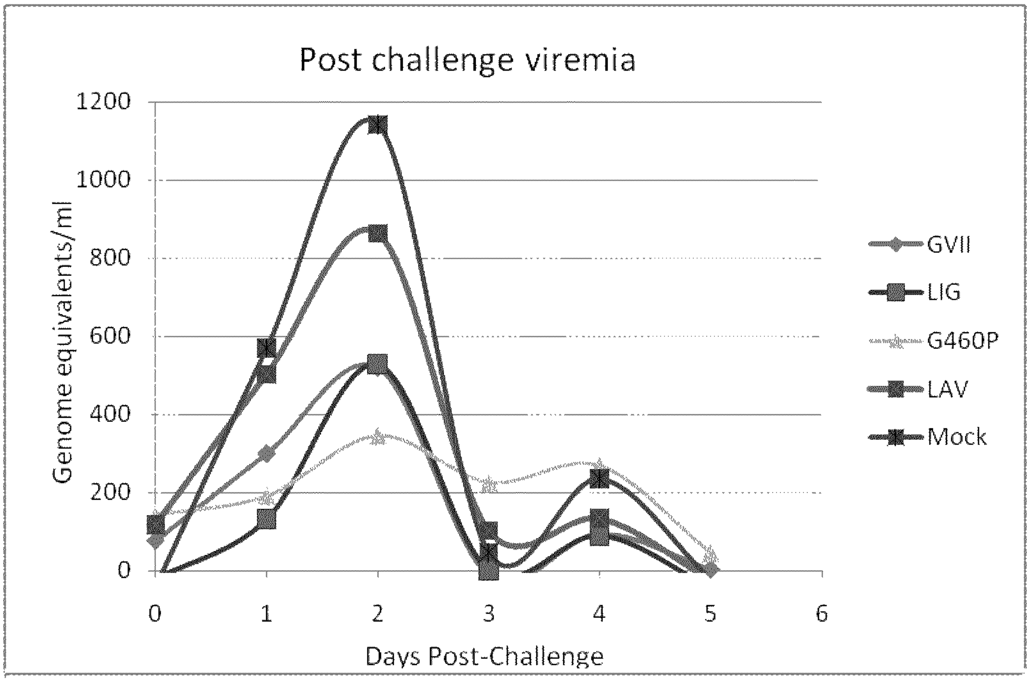
FIG. 2. Assessment of post-challenge viremia in African green monkeys. Monkeys were initially treated with a negative control, vaccine strain 16803 variant LAV, or the experimental G460P vaccine. On day 60, the monkeys were challenged with live DEN-2 challenge virus (strain S16803 wild type; 4-5 log 10 PFU per animal). The day 1 data point represents the first day post-challenge, which correlates with day 61 of the study. Each experimental group contained 4 monkeys, and the data points shown represent the average of the viremia measurements in genome equivalents/mL observed for all monkeys in each group.

Data showing post-challenge virus viremia are depicted in FIG. 2. Plotted are the average viremia measurements in all four monkeys of each of the experimental groups, as determined by real time qRT-PCR on days 1, 2, 3, 4, and 5 post challenge. All experimental groups experienced viremia as measured by genome equivalents/mL. However, the mock vaccination group and the LAV control group produced the highest viremia. As shown in FIG. 2, the monkeys treated with the G460P experimental vaccine demonstrated less virus replication/viremia of the challenge virus. Of note, the G460P mutant produced a delayed viremia (day 3 vs. day 1) as was seen by vaccine viremia assays (data not shown). These data demonstrate the efficacy of the G460P vaccine in protecting against the viremia and viral replication associated with infection by the DEN2 virus.

Safety of the G460P vaccine was assessed by clinical observations performed from baseline until completion of the in vivo studies on study day 74, as well as determination of CBCs (complete blood counts) at baseline and on study days 30 and 60. No major clinical concerns related to experimental vaccine were identified as part of the performed assessments. For example, no erythema was observed at the injection sites, and no fever was observed in the days following experimental vaccine administration. A transient spike in body temperature was observed following viral challenge in the G460P treatment group, but this effect resolved within 48-72 hours, and no other clinical abnormalities were observed during this time. Minor changes in specific CBC measures were noted. However, such changes, which included reduced platelet counts, were not consistent with a vaccine-specific safety concern because similar findings were observed in control groups.

Monkeys were tested to evaluate viremia, antibody responses, vaccine delivery, and response to subsequent challenge with live virus. Clinical observations were made over the initial 3 days following vaccine delivery and again after the viral challenges were performed in the same animals. No increases in body temperatures were observed following subcutaneous delivery of the G460P experimental vaccine or administration of LAV or the negative control (data not shown). Similarly, no major changes in heart rate or respiratory rate were observed as a result of experimental vaccine administration compared to control groups (data not shown).

Clinical observations made after viral challenge at day 60 highlighted modest but significant differences between treatment groups. Minimal body temperature increases were observed in the initial 4 days following viral challenge across all treatment groups. On day 65 (5 days post-viral challenge), a spike in temperatures was observed for animals that had received the experimental vaccine (data not shown). Body temperatures steadily declined, approaching baseline levels over the next 2-3 days. By day 142, the challenge levels for the G460P vaccine remained high.

Overall, the clinical observations revealed no significant safety concerns and demonstrate the usefulness of the G460P vaccine in animals, including other mammals, such as humans. While not wishing to be bound by any particular theory, it is believed that because the modified G460P virus is severely impaired in mammalian systems, the mammal has sufficient time to develop immunity to the DEN2 virus in the absence of viral disease. Moreover, the fact that the G460P vaccine did not require a boost immunization further demonstrates its effectiveness and usefulness.

Methods

Focus Assays.

A focus assay was performed as a colorimetric assay or fluorescent assay using antibodies labeled with either HRPO (color substrate) or Alexa Fluor® fluorescent dye. For the color assay, the plates with transfected or infected cells are washed twice with 1×PBS and fixed with 80% methanol for 15 minutes at room temperature, followed by incubation with the antibody dilution buffer (5% skim milk in 1×PBS-D) for 10 min. The primary antibody to the Dengue virus NS1 glycoprotein (Abcam, ab41623) is added at a dilution of 1:400 in Ab dilution buffer and incubated for 1 hr at 37° C. with slow rocking. The wells are then washed twice with PBS buffer followed by the addition of secondary antibody conjugated with horse radish peroxidase (HRP) (Sigma #8924) at a dilution of 1:500 in Ab dilution buffer. Wells are washed again twice with PBS. The foci are visualized by adding 150 μl of True Blue peroxidase substrate (KPL#50-78-02) to each well and developing it for ~15 min. Foci are counted and a titer determined in focus forming units/ml (ffu/mL) of virus. For the fluorescent assay, the assay is essentially as described above with the exception that the secondary Ab is Alexa Fluor® 488 fluorescent dye $F(ab')_2$ fragment of goat anti-mouse IgG (Invitrogen # A-11017, Carlsbad, Calif.) diluted 1:100 in Ab dilution buffer. This assay is read as a $TCID_{50}$ assay (Hernandez et al., 2005), and is the method of choice when the foci are too small to be counted accurately by the colorimetric assay.

Infection and purification of selected mutants. The WT virus and the mutant DV2 viruses were grown in the *Aedes albopictus* derived C6/36 cell line. The cells were split one day before infection at a ratio of 1:3. Subconfluent monolayers of C6/36 cells will then be infected at ~MOI of 0.03. Virus was diluted in the C6/36 media and each 75 $cm^3$ flask infected with 1.0 ml of diluted virus for 1 hr at room temperature with slow rocking 4.0 ml of fresh media is added to each flask and incubated at 28° C. for 7 days. Virus was harvested by centrifugation of the supernatant at 4000 rpm for 10 min. The following method was used to achieve the highest purity. The Dengue mutant virus was harvested 6-7 days after infecting 50-75 $cm^2$ flasks of C6/36 cells (5 ml total volume/flask). The 250 ml of virus in media was prefiltered through a Millipore™ fiber glass filter. The pre-filtered virus supernatant was run through a clean 1,000 kDa MWCO Tangential flow filter (TFF) (Millipore, Conn.), and concentrated to a final volume of 40 ml. The 40 ml of virus supernatant from the TFF was loaded onto ultracentrifugation gradients. Gradients consisted of a 12% to 35% optiprep (Optiprep, Sigma, St. Louis Mo.) solution step, in PBS-D with 10 mM Tris-HCl, and 1 mM EDTA. The virus was spun to equilibrium in 35%-12% Iodixanol gradients. Blue virus bands were collected from the first series of optiprep gradients, and diluted 1:1 with PBS-D, 10 mM Tris-HCl, and 1 mM EDTA. The diluted 1× purified virus samples were loaded onto a smaller second ultracentrifuge gradient of the same composition as the first. The small concentrated blue band of virus was collected from the second gradient. Protein concentration was determined using BCA, and 15 μl of each purified virus sample was run on a 4-12% bis-tris gel.

RT-PCR Analysis of Mutant Viruses.

To confirm that the desired mutations remained in the virus grown in cell culture, the RNA was extracted from the mutant viruses, reverse transcribed, and amplified by PCR (RT/PCR). RNA extraction was done by two methods. The first method involved extracting RNA from a minimum of $10^4$ PFU of virus by pelleting the virus at 50,000 rpm in a SW55Ti (Beckman Coulter, Fullerton Calif.) rotor for 1 hour. The pelleted virus was extracted as described previously (Hernandez et al., 2000). The RNA pellet was resuspended in 10 μl of diethyl pyrocarbonate (DEPC) treated water and checked on 1% agarose gel. The second method involved extracting the RNA from the C6/36 cells infected by the mutant viruses by RNeasy Mini kit (Qiagen, Valencia, Calif.). This method of RNA extraction was used when the titer of the mutant virus was low. In brief, the infected cells were scraped off from the flasks on Day 7 and suspended in media at the cell density of $\sim 1\times 10^7$ cells. Cells were spun down and resuspended in the lysis buffer, homogenized and the RNA purified using the RNeasy mini kit. RNA was suspended in 30 μl of RNase free water and checked on a 1% agarose gel. The extracted RNA by either of the methods was reverse transcribed and amplified by PCR by One-Step RT-PCR kit (Qiagen, Valencia Calif.). The primers designed for use in the RT-PCR reaction were compared with folded RNA structures to optimize RNA accessibility (Mathews et al., 1999). The products generated in the RT-PCR reaction (~640 bp) are phenol/chloroform extracted, precipitated and sequenced to confirm the mutations. Some of the RT-PCR products are insufficient to be sequenced directly. These products are amplified by nested PCR, subcloned in pDrive cloning vector and transformed in QIAGEN EZ Competent cells using the QIAGEN PCR cloning$^{plus}$ kit. The white colonies with the ligated product are grown and the miniprep DNA is sequenced for mutations (Eurofins MWG Operon, Huntsville, Ala.).

Infectious Center Assay.

The following method was used to purify all mutant virus from any contaminants. Virus amplified from the infections was amplified by RT-PCR and sequenced, and it was confirmed that all mutant virus exhibited the correct sequence. Approximately 2 ml/well of a 1:1 ratio solution of 2×MEM and 2% agarose was placed in each well of 6-well plates. Density of C7-10 cells was counted and calibrated. C7-10 cells were centrifuged to obtain $>5\times 10^6$ cells per well. The C7-10 cells were then resuspended in 1 ml of media/well ($5\times 10^6$ cells/ml). Virus (or sera) was diluted in serial 1:10 dilutions in 1×MEM complete. 2 ml of cell solution (enough cells to plate 2 wells) was infected with 250 μl of each virus dilution in 5 ml Corning tubes. The samples were rocked at room temperature for 1.5 hours. 2.8% soft agarose (SeaPlaque Agarose "low gelling temp." FMC BioProducts) was melted in the microwave, and combined 1:1 with 2×MEM complete media. 2 ml soft agarose/media solution was added to each tube of infected cells. 2 ml of infected cell/soft agarose mixture (in duplicate) were placed into each well of the six well plates, making sure to keep track of the dilution factor. 3 days post infection, infectious center formation can be observed in the 3 dimensional cell layers in the soft agar. When infectious centers are visible, approximately 5 days post infection, the plates are stained using neutral red. Staining is performed by missing 2×MEM complete and 2% agarose 1:1, adding 3% of the lab neutral red stock solution, and plating approximately 2 ml/well. To purify and evaluate the virus, infectious centers that are visibly separate after neutral red has been absorbed are chosen, and all solid material surrounding the infection is removed. The virus is then eluted into 1 ml diluent for 2 days at 4° C. and amplified in C6/36 cells.

Transmission Electron Microscopy.

Vero or C6/36 cells were transfected with RNA transcribed from either WT Dengue 2 or individual mutants. Incubation proceeded at 37° C. for 16-18 hours, after which the cell monolayers were scraped from the flasks and pelleted by low speed centrifugation. Cell pellets were washed twice with PBS and fixed with 3% glutaraldehyde (Ladd Research Industries, Inc. Williston, Vt.) in 0.1M cacodylic acid buffer pH 7.4 (Ladd Research Industries). After cells were washed 3 times with 0.1M cacodylic acid, the cells were stained with 2% osmium tetroxide in cacodylic buffer for 1 hour. Cells were then washed as before and embedded in 2% agarose. The agarose containing the cell sample was then pre-stained with 1% uranyl acetate (Polaron Instruments, Inc, Hatfield, Pa.) overnight at 4° C. The samples were washed and carried through ethanol dehydration. Infiltration was done using SPURR compound (LADD Research Industries). Blocks were then trimmed on an LKB NOVA Ultrotome (Leica Microsystems, Inc. Deerfield, Ill.). Ultra-thin sections were then obtained and stained with 5% uranyl acetate in distilled water for 60 minutes and in Reynolds lead citrate pH 12 (Mallinkrodt, Baker Inc. Paris, Ky.) for 4 minutes. The samples were examined at 80 kV in a JEOL JEM 100S transmission electron microscope.

African Green Monkey Vaccine Experiments.

Serum samples were collected and clinical observations made at baseline and at 1, 2, 3, 5, 7, 14, 30, and 60 days after vaccine administration. After serum collection on day 60, animals received live DEN-2 challenge virus (strain 16803 wild type obtained from Robert Putnak of the WRAIR (Eckels et al., 2003); 4-5 log 10 PFU per animal) before continued serum collection and clinical observations at 61-67 and 74 days after vaccine administration. All animals were prescreened for the presence of anti-Dengue 1-4 IgM or IgG. Four monkeys were included in each experimental group—four monkeys were administered the G460P vaccine, four were administered cell supernatant from uninfected C6/36 cells and served as negative controls, and four were administered LAV and served as positive controls. Cell supernatant from uninfected C6/36 cells was used as the control inoculum to control for the effect of mosquito antigens on the animals.

The study design was based on other studies performed in the African green monkey (Martin et al., 2009; Martin et al., 2009) and rhesus monkey (Halstead et al., 1973). Table 5 illustrates the study design. No virus boost was incorporated because it was expected that the vaccine strains would generate sufficient viremia so as not to require a second dose. Indeed, no virus boost was required.

TABLE 5

Study Design

| Study day | Event | plasma volume (Cumulative vol.) |
|---|---|---|
| Day 0 | Blood sample for baseline dengue antibody<br>Baseline PCV/Hematocrit (RxGEN)<br>First vaccine dose | 5 ml (5 ml) |
| Day 1 | Animal observation (including injection site)<br>Blood sample for vaccine viremia | 2 ml aliquot samples (7 ml) |
| Day 2 | Animal observation (including injection site)<br>Blood Sample for vaccine viremia | 2 ml aliquot (9 ml) |

TABLE 5-continued

| Study Design | | |
|---|---|---|
| Study day | Event | plasma volume (Cumulative vol.) |
| Day 3 | Blood sample for vaccine viremia | 2 ml (11 ml) |
| Day 4 | Observation | — |
| Day 5 | Blood sample for IgM antibody, viremia | 2 ml (13 ml) |
| Day 7 | Blood sample for IgM antibody, viremia | 2 ml (15 ml) |
| Day 14 | Blood sample for IgG antibody | 2 ml (17 ml) |
| Day 30 | Blood sample for IgG antibody PCV/Hematocrit (RxGEN) | 2 ml (19 ml) |
| Day 60 | Blood sample for IgG antibody PCV/Hematocrit (RxGEN) Virus Challenge | 2 ml (21 ml) |
| Day 61-70 | Blood samples collected for 10 consecutive days for WT virus viremia measurement | 20 ml, 2 ml per day (41 ml) |
| Day 75 | Blood sample for IgG antibody Study termination | 2 ml (43 ml) |
| | Total blood volume drawn (75 Study Days) | 43 ml |

Vaccine strains or controls were administered in 0.5 mL iodixanol solution (33% in PBS-D) after concentration by tangential flow filtration (TFF) and purification on 12% and 35% step iodixanol gradients to remove serum albumin and further concentrate the virus. The dose of the DV2G460P vaccine strain was $7.5\times10^4$ ffu/monkey. A single vaccination with no boost was given via subcutaneous injection. The positive control, derivative LAV (strain 16803) was obtained from Robert Putnak of the WRAIR (Eckels et al., 2003). Table 6 shows the virus titers used for the wild-type and mutant virus. Table 6 includes titers used for the following additional control strains: the DV216681 strain, which is the parent strain that was used to make the mutant G460P virus, and the DV216803 strain, which is an attenuated LAV derivative strain that was also obtained from Robert Putnak of the WRAIR (Eckels et al., 2003).

TABLE 6

| Virus titers for the DEN-2 WT virus and mutant viruses | | | |
|---|---|---|---|
| | | Titer (ffu/mL) | |
| Virus | E-T1 Sequence | Vero | C6/36 |
| DV216681 | SWTMKILIGVIITWIG | $1 \times 10^6$ | $1 \times 10^7$ |
| DV2G460P | SWTMKILIPVIITWIG | $2.5 \times 10^1$ | $5 \times 10^2$ |
| DV216803 LAV (attenuated) | SWTMKILIGVIITWIG | $1.0 \times 10^{4-5}$ | ND |
| DV216803 (wild-type) | SWTMKILIGVIITWIG | $1.0 \times 10^{4-5}$ | ND |

Days 1, 2, 3, 5, and 7 post-inoculation were chosen to assay for viremia. An assay of infectious centers was chosen over a plaque assay because the infectious center assay is more sensitive. Assay for the production of neutralizing IgM and IgG titers began on day 5 post-injection samples and included days 7, 14, and 30. Three different assays to test for Ab production were performed on each individual sample in each group on the days reported.

Safety was assessed by clinical observations (e.g., assessing complete blood count (CBC) and body temperature) performed from baseline until completion of in vivo studies on study day 74 as well as determination of CBCs at baseline and on study days 30 and 60. Viremia and antibody responses were assessed to test vaccine delivery and response to subsequent challenge with live virus. Clinical observations were made over the initial 3 days following vaccine delivery and again after the viral challenges were performed in the same animals. Body temperature was determined using a rectal thermometer as part of the clinical observations.

Example 3

DEN-1, DEN-3, and DEN-4 Mutants

DEN-1, DEN-3, and DEN-4 host-range mutants were created and may be utilized in the compositions and methods disclosed herein. Table 7 provides the DEN-1, DEN-3, and DEN-4 mutants that were created:

TABLE 7

| DEN-1, DEN-3, and DEN-4 mutants | | |
|---|---|---|
| | E-T1 Domain Sequence | Proline Substitution |
| DEN1 | $_{452}$SWTMKIGIGILLTWLG$_{467}$ (SEQ ID NO: 15) | $G_{460}P$ |
| DEN3 | $_{448}$SWIMKIGIGVLLTWIG$_{465}$ (SEQ ID NO: 16) | $G_{458}P$ |
| DEN4 | $_{452}$SWMIRILIGFLVLWIG$_{467}$ (SEQ ID NO: 17) | $G_{460}P$ |

The DEN-1, DEN-3, and DEN-4 host-range mutants are produced and tested as described above for the DEN-2 G460P mutant. As with the DEN-2 G460P mutant, the proline substitution mutation introduces a kink in the transmembrane domain of the virus, thus shortening the transmembrane domain. Thus, like the DEN-2 G460P mutant, it is expected that the DEN-1 G460P, DEN-3 G458P, and DEN-4 G460P mutants will be capable of replicating and assembling normally in an insect host cell, but will assemble poorly in a mammalian host cell. These additional host-range mutants are expected to be useful in vaccine compositions and to produce immunity to wild-type virus infection when used in a vaccine.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932

U.S. Pat. No. 3,949,064

U.S. Pat. No. 4,174,384

Adams and Rose, *Cell,* 41(3):1007-1015, 1985.

Amberg et al., *J. Virol.,* 73:8083-8094, 1999.

Bowers et al., *Virology,* 212(1):1-12, 1995.

Bretscher and Munro, *Science,* 261:1280-1, 1993.

Brown and Condreay, In: *The Togaviruses and Flavivirlia.* Schlesinger et al. (Eds.), 11(2/3):225-237, Plenum Press, NY, 1986.

Ceruso and Weinstein, *J. Mol. Biol.,* 318(5):1237-1249, 2002.

Clayton, *J. Lipid. Res.,* 15:3-19, 1964.

Condreay and Brown, *J. Virol.,* 58:81-6, 1986.

Eckels et al., *Am. J. Trop. Med. Hyg.,* 69:12-16, 2003.

Edwards and Brown, *Virology,* 182(1):28-33, 1991.

Gresikova et al., In: *The Arboviruses, Ecology and Epidemiology*, Monath (Ed.), CRC Press, Boca Raton, Fla., IV:177-203, 1988.

Halstead et al., *J. Infect. Dis.,* 128:15-22, 1973.

Hernandez et al., *Curr. Protoc. Microbiol.,* 15:15B-1, 2005.

Hernandez et al., *J. Virol.,* 74:4220-8, 2000.

Hernandez et al., *J. Virol.,* 77(23):12710-9, 2003.

Irie et al., *Gene,* 75:197-211, 1989.

Klaassen, In: *The Pharmacological Basis of Therapeutics*, Goodman and Gilman (Eds.), Pergamon Press, 8$^{th}$ Ed., 1990.

Lobigs and Lee, *J. Virol.,* 78:178-86, 2004.

Lobigs et al., *Immunol. Cell Biol.,* 82:184-8, 2004.

Martin et al., *Curr. Microbiol.,* 59:579-83, 2009.

Martin et al., *Microbiol. Immunol.,* 53:216-23, 2009.

Martina et al., *Clin. Microbiol. Rev.,* 22:564-581, 2009.

Mathews et al., *J. Mol. Biol.,* 288:911-40, 1999.

Mitsuhashi et al., *Cell Biol. Int. Rep.,* 7(12):1057-62, 1983.

Monath, In: *The Togaviridae and Flaviviridae*, Schlesinger et al. (Eds.), 375-440, Plenum Press, NY, 1986.

Mukhopadhyay et al., *Nat. Rev. Microbiol.,* 3:13-22, 2005.

Murray et al., *Nat. Rev. Micro.,* 6:699-708, 2008.

Remington's Pharmaceutical Sciences, 18th Ed. Mack Printing Company, 1990.

Rice et al., *J. Clin. Invest.,* 70(1):157-67, 1982.

Rice, In: *Virology*, Fields (Ed.), Raven-Lippincott, NY, I:937, 1995.

Rost et al., *Nucl. Acids Res.,* 32:W321-326, 2004.

Sambrook et al., In: *Molecular Cloning: a Laboratory Manual,* 2$^{nd}$ Ed., Cold Spring Harbor Laboratory Press, Cold Spring Harbor, N.Y., 1987.

Samsa et al., *PLoS Pathog.,* 5:e1000632, 2009.

Schlesinger and, Schlesinger, In: *Virology,* 2$^{nd}$ Ed., Fields et al. (Ed.), Raven Press, NY, 697-712, 1990.

von Heijne, *J. Mol. Biol.,* 218(3):499-503, 1991.

West et al., *J. Virol.,* 80:4458-68, 2006.

WHO, W.H.O. *Vector-borne viral infections,* 2009.

Zhang et al., *Biologicals,* 22:205-13, 1994.

Zhang et al., *Nat. Struct. Biol.,* 10:907-12, 2003.

What is claimed is:

1. A modified flavivirus envelope protein (E) comprising a E protein N-terminal transmembrane domain (E-T1 domain) having at least one mutation relative to wild type E-T1, such a mutation consisting of a proline substituted for the central glycine, which is designated as position 0 wherein a flavivirus comprising the modified flavivirus E protein has an ability to infect mammalian cells but a reduced ability to replicate therein relative to the wild-type flavivirus.

2. The modified flavivirus envelope protein of claim 1, wherein the modified flavivirus E protein is a modified E protein of Dengue virus (DV), West Nile virus (WNV), yellow fever virus (YFV), Japanese encephalitis virus (JEV), tick-borne encephalitis virus (TBE virus), Murray Valley encephalitis virus (MVEV), Saint Louis encephalitis virus (SLEV), or Powassan virus (PV).

3. The modified flavivirus envelope protein of claim 2, wherein the modified flavivirus E protein is a modified E protein of Dengue virus.

4. The modified flavivirus envelope protein of claim 3, wherein the modified flavivirus E protein is a modified E protein of Dengue virus type 2.

5. The modified flavivirus envelope protein of claim 4, wherein the mutation comprises a proline at amino acid position 460.

6. The modified flavivirus envelope protein of claim 3, wherein the modified flavivirus E protein is a modified E protein of Dengue virus type 1.

7. The modified flavivirus envelope protein of claim 6, wherein the mutation comprises a proline at amino acid position 460.

8. The modified flavivirus envelope protein of claim 3, wherein the modified flavivirus E protein is a modified E protein of Dengue virus type 3.

9. The modified flavivirus envelope protein of claim 8, wherein the mutation comprises a proline at amino acid position 458.

10. The modified flavivirus envelope protein of claim 3, wherein the modified flavivirus E protein is a modified E protein of Dengue virus type 4.

11. The modified flavivirus envelope protein of claim 10, wherein the mutation comprises a proline at amino acid position 460.

12. The modified flavivirus envelope protein of claim 2, wherein the modified flavivirus E protein is a modified E protein of West Nile virus.

13. The modified flavivirus envelope protein of claim 12, wherein the mutation comprises a proline at amino acid position 465.

14. The modified flavivirus envelope protein of claim 1, wherein the mammalian cells are human cells.

15. The modified flavivirus envelope protein of claim 1, wherein a virus comprising the modified flavivirus E protein has an ability to produce at least 100 fold more progeny virus when infecting insect cells than when infecting mammalian cells.

16. The modified flavivirus envelope protein of claim 1, wherein a virus comprising the modified flavivirus E protein has an ability to produce at least 1000 fold more progeny virus when infecting insect cells than when infecting mammalian cells.

17. An engineered nucleic acid encoding the modified flavivirus envelope protein of claim 1.

18. A genetically engineered flavivirus comprising at least the engineered nucleic acid of claim 17.

19. An immunogenic composition comprising the genetically engineered flavivirus of claim 18.

20. The immunogenic composition of claim 19, wherein the composition comprises one or more of a genetically engineered Dengue virus type 1, 2, 3, and 4.

21. The immunogenic composition of claim 20, wherein the vaccine composition comprises a genetically engineered Dengue virus type 2.

22. The immunogenic composition of claim 20, wherein the composition is a tetravalent vaccine composition comprising the genetically engineered Dengue virus types 1, 2, 3, and 4.

23. The immunogenic composition of claim 19, further comprising an adjuvant or a preservative.

* * * * *

UNITED STATES PATENT AND TRADEMARK OFFICE

CERTIFICATE OF CORRECTION

PATENT NO. : 8,889,148 B2
APPLICATION NO. : 13/173895
DATED : November 18, 2014
INVENTOR(S) : Dennis T. Brown and Raquel Hernandez It is certified that error appears in the above-identified patent and that said Letters Patent is hereby corrected as shown below:

In the Claims,

In claim 21, column 38, line 55, delete "vaccine".

Signed and Sealed this
Fourteenth Day of April, 2015

Michelle K. Lee

Michelle K. Lee
*Director of the United States Patent and Trademark Office*